Figure 1:
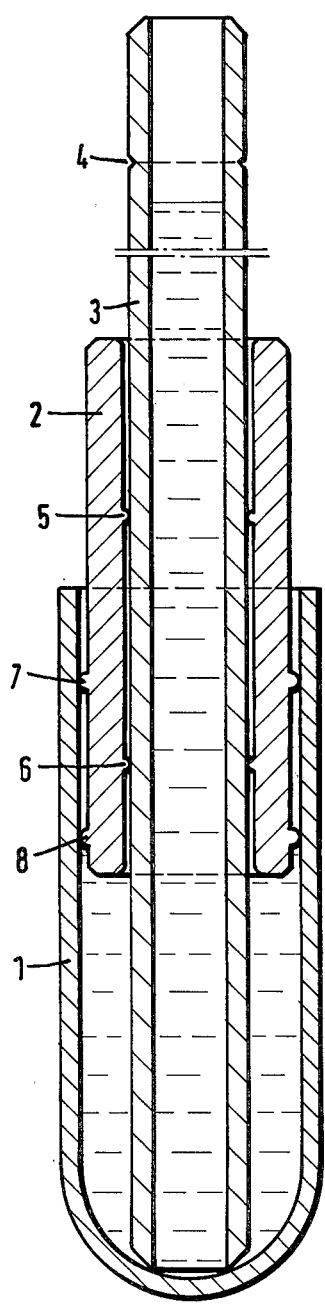

United States Patent [19]

Färber et al.

[11] 4,353,246

[45] Oct. 12, 1982

[54] BLOOD SEDIMENTATION DEVICE

[75] Inventors: Horst Färber, Nümbrecht; Heinz Fritze, Gummersbach; Eberhard Seibel, Waldbröl, all of Fed. Rep. of Germany

[73] Assignee: Walter Sarstedt Kunststoff-Spritzgusswerk, Nümbrecht, Fed. Rep. of Germany

[21] Appl. No.: 178,910

[22] Filed: Aug. 18, 1980

[30] Foreign Application Priority Data

Sep. 1, 1979 [DE] Fed. Rep. of Germany ....... 2935371

[51] Int. Cl.$^3$ ............................................. G01N 15/04
[52] U.S. Cl. .................................. 73/61.4; 210/359; 210/927
[58] Field of Search ................. 73/61.4, 61 R, 864.24; 210/359, 927

[56] References Cited

U.S. PATENT DOCUMENTS 3,512,940  5/1970  Shapiro ............................ 73/61 R
4,197,735  4/1980  Munzer et al. .................... 73/61.4

Primary Examiner—Anthony V. Ciarlante
Assistant Examiner—Joseph W. Roskos
Attorney, Agent, or Firm—Browdy and Neimark

[57] ABSTRACT

A blood sedimentation device has a transparent small-diameter sedimentation tube and is provided with a calibration mark a short distance below its upper end. The column of blood is introduced into the sedimentation tube and is precisely bounded at the lower end of the tube. The device has a displacement sleeve surrounding the lower part of the sedimentation tube in an airtight manner allowing movement by sliding, and further has a tubular receptacle, closed at the bottom, surrounding the displacement sleeve in an airtight manner allowing movement by sliding, this receptacle accomodates the blood sample.

5 Claims, 2 Drawing Figures

BLOOD SEDIMENTATION DEVICE

The invention relates to a blood sedimentation device, comprising a transparent small-diameter sedimentation tube, provided with a calibration mark a short distance below its upper end. A sedimentation tube of this type is filled with blood, up to the upper calibration mark, and then placed in a vertical position. In the blood, which has previously been rendered non-coagulating in a known manner, the red blood corpuscles now gradually settle out, with the result that the blood serum remains in the upper space. The boundary between the lower portion, which contains the blood corpuscles, and the overlying blood serum is observed after a certain time, or at certain time intervals, and the sedimentation rate thereby indicated is used for diagnostic purposes.

In order to be able to carry out comparable measurements, the column height in the sedimentation tubes must be the same for all samples. This is achieved by filling up to the calibration mark at the upper end of the sedimentation tube. At the same time, the bottom of the fluid column must be precisely bounded. In the case of a known blood sedimentation device, this is achieved by means of a closure piece at the lower end of the sedimentation tube, this closure piece having a valve, which is closed after introducing the blood from the side, by means of a syringe, or the like.

On account of the valve, this known blood sedimentation device is expensive, and is accordingly used many times over, but the cleaning operations are time-consuming.

Another blood sedimentation device has been disclosed, which has a plastic filling-cap, into which the sedimentation tube, provided with its calibration mark, is pushed in an airtight manner. The sedimentation tube is pushed into this filling-cap as far as its lower end, so that the bottom of the blood column is thereby bounded in a precise manner. At the same time, the blood in the filling-cap is displaced by the insertion of the sedimentation tube and escapes upwards via the bore of the tube.

There is also a calibration mark in the filling-cap, and it is necessary to fill the filling-cap exactly up to this calibration mark. The volume of blood then introduced is such that, when the associated sedimentation tube is pushed in, the blood rises to the calibration mark at its upper end. This requires that the filling-cap be filled with the blood in a very precise manner. Moreover, the sedimentation tubes used must be accurately sized, not only with regard to their internal diameter, that is, with regard to their filling volume, but also with regard to their wall thickness, since the displacement action must be completely reproducible.

Nevertheless, the manufacturer of this blood sedimentation device does not exclude the possibility that the blood rises beyond the calibration mark as the sedimentation tube is pushed in. In order to correct this, some venting is possible, in the case of the known device, by laterally bowing the sedimentation tube within the somewhat elastic filling-cap. If however, in doing this, the blood level again falls below the calibration mark, no further correction is possible and the entire procedure must be repeated, by pulling out the sedimentation tube, refilling with blood, followed by reinsertion of the sedimentation tube. Although this known device is less expensive than the valve-equipped blood sedimentation devices initially mentioned, it is nevertheless, for this reason, troublesome to handle.

The object of the invention is to produce a blood sedimentation device of the type initially mentioned, which is simple and cheap to manufacture and, additionally, is simple to use and involves no special requirements with regard to the uniformity of the wall thickness of the blood sedimentation tube.

This object is achieved, according to the invention, by surrounding the lower part of the blood sedimentation tube by a displacement sleeve, in an airtight manner allowing movement by sliding, this sleeve being in turn surrounded, in an airtight manner allowing movement by sliding, by a tubular receptacle, closed at the bottom, this receptacle accommodating the blood sample.

The receptacle is filled with blood, accurate metering-in being unimportant. The lower end of the sedimentation tube is then pushed into this receptacle, whilst the displacement sleeve may already be positioned on the sedimentation tube, above its lower end. It is advantageous for the distance between the lower rim of the sedimentation tube and the lower rim of the displacement sleeve to be approximately equal to the height of the receptacle, or a little less. If the sedimentation tube is now introduced into the receptacle, which is filled with blood, the lower rim of the displacement sleeve is located approximately at the upper rim of the receptacle, or already slightly enters the receptacle. As soon as the sedimentation tube rests on the bottom of the receptacle, the displacement sleeve is pushed further into the receptacle. At the same time, it displaces part of the blood contained in the receptacle, this blood forcing its way through the gap which is always present between the sedimentation tube and the receptacle, this gap resulting from irregularities in the lower rim of the sedimentation tube, and rises inside the sedimentation tube. The displacement sleeve is moved downwards until the blood in the sedimentation tube has reached the calibration mark at its upper end. If, in doing so, the displacement sleeve has been moved rather too far downwards, so that the blood rises beyond the calibration mark, this error can be corrected without difficulty, by carefully moving the displacement sleeve upwards again, while at the same time, however, the sedimentation tube must be firmly held, so that it still rests on the bottom of the receptacle.

The receptacle is advantageously manufactured from a transparent material, glass or plastic for example, and it can also be provided with a calibration mark, so that only sufficient blood is introduced as is necessary to ensure proper adjustment.

The displacement sleeve is manufactured, as appropriate, from a material possessing a relatively low modulus of elasticity, so that it seals, internally and externally, by virtue of its elasticity. Preferably, however, sealing-lips are formed on the inner wall and/or the outer wall of the displacement sleeve.

In order to provide the sedimentation tube with lateral guidance on the bottom of the wider receptacle, thus facilitating subsequent handling of the device, a funnel-shaped narrowing is provided on the inside of the receptacle, at the bottom. This narrowing can also be produced by placing a ring-shaped insert in the receptacle, this insert having a funnel-shaped widening.

In a further development of the invention, an external thread is applied to the upper end of the receptacle and the displacement sleeve is provided with a flange and, integrally attached thereto, an adjusting collet, which surrounds the displacement sleeve with a clearance and is provided with an internal thread which matches the external thread on the upper end of the receptacle. The relative arrangement then allows, after the sedimentation tube comes to rest on the bottom of the receptacle, the displacement sleeve first to be pushed downwards, by gripping its flange or the surrounding adjusting collet, by an amount such that the blood rises in the sedimentation tube to a level just below the calibration mark. In this predetermined location of the parts relative to each other, the thread of the adjusting collet engages into the external thread of the receptacle. Further downward movement of the displacement sleeve can then be effected by turning the adjusting collet. Extremely sensitive setting of the blood level in the sedimentation tube, to the height of the calibration mark, is rendered possible by turning the collet in this manner.

Figure 2:
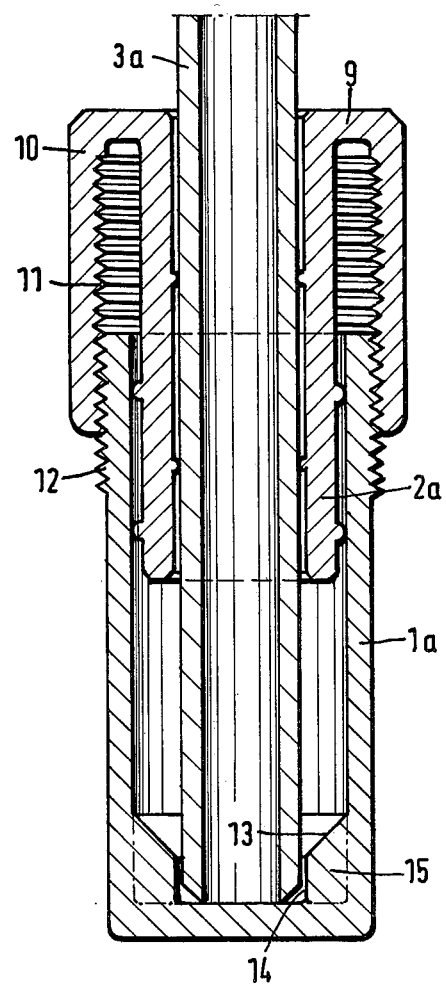

In the following text, the invention, in the form of illustrative embodiments, is explained in greater detail with the aid of the drawing, in which:

FIG. 1 shows a section through a blood sedimentation device according to the invention, in operation, and FIG. 2 shows a section through a modified embodiment.

The device represented in FIG. 1 consists of a tubular receptacle 1, made of transparent plastic and closed at the bottom, a sedimentation tube 3, made of glass and open at both ends, having a calibration mark 4 below its upper end, and a displacement sleeve 2, made of plastic possessing a low modulus of elasticity, this sleeve being located between the receptacle 1 and the sedimentation tube 3.

On its inner wall, the displacement sleeve is provided with two sealing-lips 5 and 6. Similarly, two sealing-lips 7 and 8 are located on the outer surface of the displacement sleeve 2. The displacement sleeve 2 can easily be moved, relative to the sedimentation tube 3 and the receptacle 1, by sliding, but, by virtue of the above-mentioned sealing-lips, represents a closely fitting displacement piston, which, by downward movement, penetrates into the annular gap between the sedimentation tube 3 and the receptacle 1, and displaces the blood within this gap, so that the blood forces its way into the sedimentation tube, across its bottom edge, and correspondingly rises in the sedimentation tube. The blood level can be set to the height of the calibration mark 4 in a simple manner. If the blood level accidentally rises too high, this incorrect setting can easily be corrected by slightly moving the displacement sleeve 2 in a upward direction, while firmly holding the sedimentation tube 3.

In the embodiment represented in FIG. 2, the receptacle 1a is internally narrowed at its bottom, in a funnel-shaped manner, at 13, and, at 14, provides a guide for the sedimentation tube 3a when the latter is introduced. In place of the thickening 15, shown in FIG. 2, an appropriate ring-insert can also be employed in a receptacle according to FIG. 1.

In this embodiment, a flange 9 extends radially outwards from the upper end of the displacement sleeve 2a, this flange in turn carrying an adjusting collet 10, which concentrically surrounds the displacement sleeve 2a with a clearance. The internal diameter of the adjusting collet 10 and the external diameter of the receptacle 1a are mutually matched and the adjusting collet is provided with an internal thread, which can engage with an external thread 12 on the upper part of the exterior of the receptacle 1a. In this regard, the relative arrangement and dimensioning of the parts is designed such that, from first introducing the displacement sleeve, up to the engagement of the thread, just enough blood was displaced to reach nearly to the calibration mark on the upper part of the sedimentation tube. Subsequently, the blood level is brought exactly to the calibration mark, by turning the adjusting collet 10.

I claim:

1. A blood sedimentation device, comprising:
   a transparent small-diameter sedimentation tube, provided with a calibration mark a short distance below the upper end thereof;
   a tubular displacement sleeve disposed on said sedimentation tube, said displacement sleeve being open at both ends so as to permit said sedimentation tube to pass through and extend from both ends thereof, wherein the inner diameter of said displacement sleeve is so dimensioned relative to the outer diameter of said sedimentation tube as to frictionally engage said sedimentation tube while allowing said sleeve to be axially displaceable against the entire length of said sedimentation tube; and
   a tubular receptacle, closed at the bottom, having an inner diameter sized relative to the outer diameter of said displacement sleeve such that said displacement sleeve can be inserted in a piston-like manner into said tubular receptacle.

2. A blood sedimentation device in accordance with claim 1, wherein said displacement sleeve engages said sedimentation tube in a liquid sealing manner by means of sealing lips on the inner wall of said displacement sleeve.

3. A blood sedimentation device in accordance with claim 1, wherein said displacement sleeve engages said receptacle in a liquid sealing manner by means of sealing lips on the outer wall of said displacement sleeve.

4. A blood sedimentation device in accordance with claim 1, wherein the lower end of said receptacle has a funnel-shaped narrowing means therein for guiding and holding the bottom of said sedimentation tube.

5. A blood sedimentation device in accordance with claim 1, wherein said receptacle has an external thread thereon and wherein said displacement sleeve has an adjusting collet connected thereto provided with an internal thread corresponding to said external thread of said receptacle, whereby screwing or unscrewing said collet while firmly holding said sedimentation tube against the bottom of said receptacle causes said displacement sleeve to be displaced with respect to said sedimentation tube and said receptacle.

* * * * *